United States Patent
Munro

(10) Patent No.: US 8,648,296 B2
(45) Date of Patent: *Feb. 11, 2014

(54) SPECTROMETER APPARATUS

(71) Applicant: Smiths Detection-Watford Limited, Watford (GB)

(72) Inventor: William Angus Munro, Dunstable (GB)

(73) Assignee: Smiths Detection-Watford Limited, Watford, Hertfordshire (GB)

(*) Notice: Subject to any disclaimer, the term of this patent is extended or adjusted under 35 U.S.C. 154(b) by 0 days.

This patent is subject to a terminal disclaimer.

(21) Appl. No.: 13/850,123

(22) Filed: Mar. 25, 2013

(65) Prior Publication Data

US 2013/0248703 A1 Sep. 26, 2013

Related U.S. Application Data

(63) Continuation of application No. 13/546,823, filed on Jul. 11, 2012, now Pat. No. 8,405,023, which is a continuation of application No. 12/444,950, filed as application No. PCT/GB2007/004050 on Oct. 22, 2007, now Pat. No. 8,222,595.

(30) Foreign Application Priority Data

Oct. 22, 2006 (GB) .................................. 0620748.4

(51) Int. Cl.
*H01J 49/10* (2006.01)
*H01J 49/40* (2006.01)

(52) U.S. Cl.
CPC ............... *H01J 49/10* (2013.01); *H01J 49/403* (2013.01); *H01J 49/40* (2013.01)
USPC ............................ 250/287; 250/282; 250/288

(58) Field of Classification Search
USPC .................................. 250/281, 282, 287, 288
See application file for complete search history.

(56) References Cited

U.S. PATENT DOCUMENTS

| 3,107,966 | A | | 10/1963 | Bonhomme |
| 3,461,285 | A | | 8/1969 | Werner |
| 3,470,527 | A | | 9/1969 | Bonhomme |
| 3,787,681 | A | | 1/1974 | Brunnee et al. |
| 4,378,499 | A | | 3/1983 | Spangler et al. |
| 4,390,784 | A | | 6/1983 | Browning et al. |
| 4,551,624 | A | | 11/1985 | Spangler et al. |
| 5,083,019 | A | | 1/1992 | Spangler |
| 5,227,628 | A | | 7/1993 | Turner |
| 5,304,797 | A | * | 4/1994 | Irie et al. ......................... 250/287 |

(Continued)

FOREIGN PATENT DOCUMENTS

| EP | 0135747 | 4/1985 |
| GB | 2323165 | 9/1998 |

(Continued)

*Primary Examiner* — Jack Berman
(74) *Attorney, Agent, or Firm* — Reinhart Boerner Van Deuren s.c.

(57) ABSTRACT

An ion mobility spectrometer has several electrodes spaced along its ion source region. Voltages are applied to the electrodes to produce a voltage gradient along the length of the ion source region. By varying the voltage gradient, the residence time of ions in the ion source region can be selectively varied. Typically, the spectrometer is arranged to reduce the residence time in response to a decrease in the amplitude of an ion peak detected at the far end of the drift region.

20 Claims, 1 Drawing Sheet

(56) References Cited

U.S. PATENT DOCUMENTS

| | | |
|---|---|---|
| 5,574,277 A | 11/1996 | Taylor |
| 5,723,861 A | 3/1998 | Carnahan et al. |
| 5,854,431 A | 12/1998 | Linker et al. |
| 5,952,652 A | 9/1999 | Taylor et al. |
| 6,051,832 A | 4/2000 | Bradshaw |
| 6,073,498 A | 6/2000 | Taylor et al. |
| 6,102,746 A | 8/2000 | Nania et al. |
| 6,225,623 B1 | 5/2001 | Turner et al. |
| 6,239,428 B1 | 5/2001 | Kunz |
| 6,442,997 B1 | 9/2002 | Megerle et al. |
| 6,459,079 B1 | 10/2002 | Machlinski et al. |
| 6,481,263 B1 | 11/2002 | Haley et al. |
| 6,495,824 B1 | 12/2002 | Atkinson |
| 6,502,470 B1 | 1/2003 | Taylor et al. |
| 6,523,393 B1 | 2/2003 | Linker et al. |
| 6,825,460 B2 | 11/2004 | Breach et al. |
| 7,098,449 B1 | 8/2006 | Miller et al. |
| 7,118,712 B1 | 10/2006 | Manginell et al. |
| 7,311,566 B2 | 12/2007 | Dent |
| 8,222,595 B2 * | 7/2012 | Munro .......................... 250/287 |
| 8,405,023 B2 * | 3/2013 | Munro .......................... 250/282 |
| 2002/0150923 A1 | 10/2002 | Malik |
| 2004/0259265 A1 | 12/2004 | Bonne |
| 2005/0017163 A1 | 1/2005 | Miller et al. |
| 2005/0095722 A1 | 5/2005 | McGill et al. |
| 2005/0161596 A1 | 7/2005 | Guevremont et al. |
| 2005/0178975 A1 | 8/2005 | Glukhoy |
| 2005/0253061 A1 | 11/2005 | Cameron et al. |

FOREIGN PATENT DOCUMENTS

| | | |
|---|---|---|
| WO | WO9301485 | 1/1993 |
| WO | WO9322033 | 11/1993 |
| WO | WO9921212 | 4/1999 |
| WO | WO0079261 | 12/2000 |
| WO | WO0195999 | 12/2001 |
| WO | WO02078047 | 10/2002 |
| WO | WO2004012231 | 2/2004 |
| WO | WO2006046077 | 5/2006 |
| WO | WO2008035095 | 3/2008 |

* cited by examiner

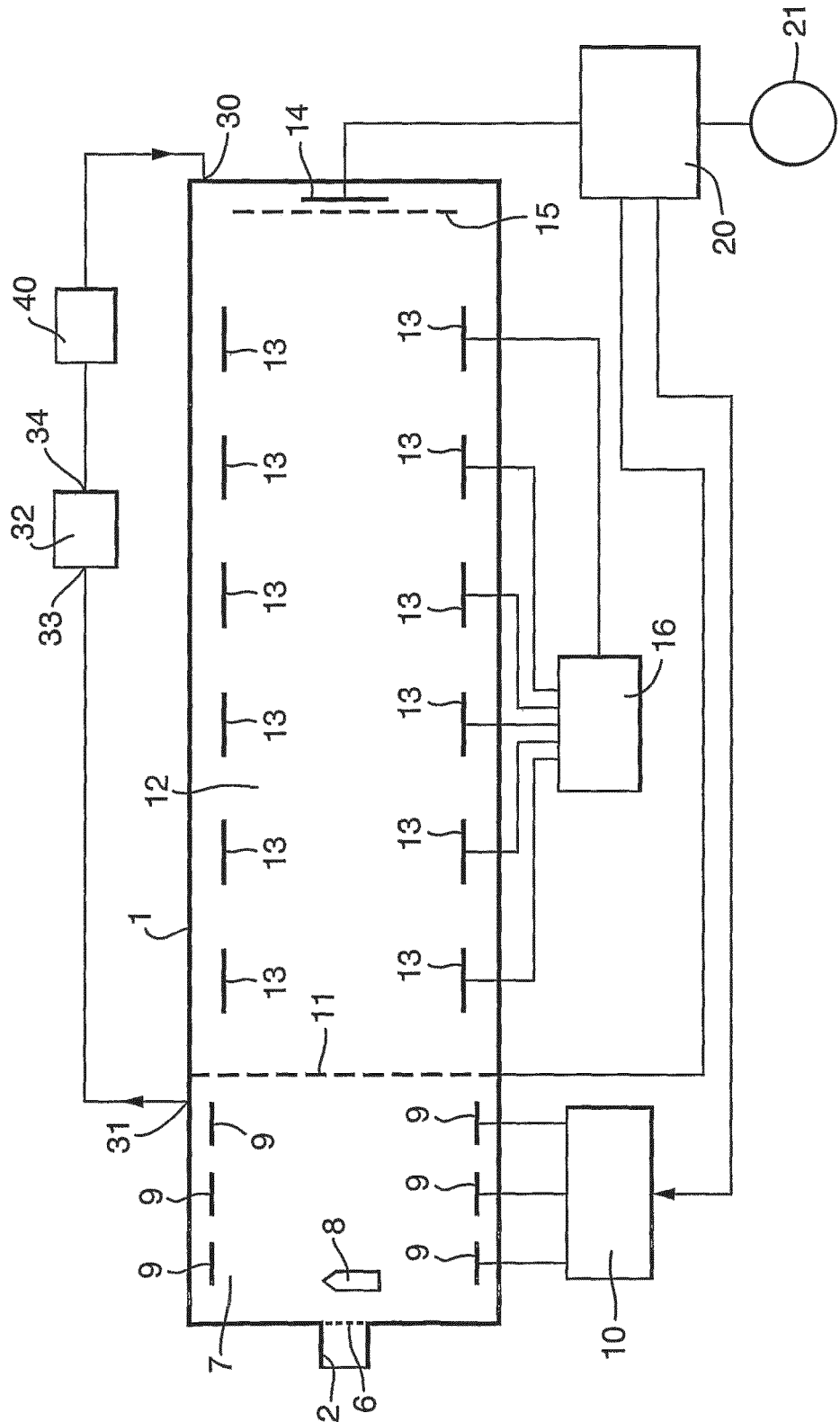

SPECTROMETER APPARATUS

CROSS-REFERENCE TO RELATED APPLICATION

This patent application is a continuation of U.S. patent application Ser. No. 13/546,823, filed on Jul. 11, 2012, entitled "Spectrometer Apparatus," now U.S. Pat. No. 8,405,023, granted on Mar. 26, 2013, which in turn is a continuation of U.S. patent application Ser. No. 12/444,950, filed on Apr. 9, 2009, entitled "Spectrometer Apparatus," now U.S. Pat. No. 8,222,595, granted on Jul. 17, 2012, which is the national entry of International Patent Application No. PCT/GB2007/004050, filed on Oct. 22, 2007, also entitled "Spectrometer Apparatus," which in turn claimed the benefit of Great Britain Patent Application No. 0620748.4, filed on Oct. 22, 2006, again entitled "Spectrometer Apparatus," all four of which are assigned to the assignee of the present invention and all four of which are hereby incorporated herein by reference in their entirety.

BACKGROUND OF THE INVENTION

Field of the Invention

The present invention relates to spectrometer apparatus of the kind having an ion source region arranged to provide ions to an analyzer region.

Ion mobility spectrometers (IMS) apparatus and field asymmetric ion mobility spectrometers (FAIMS) or differential mobility spectrometers (DMS) apparatus are often used to detect substances such as explosives, drugs, blister and nerve agents or the like. An IMS apparatus typically includes a detector cell to which a sample of air containing a suspected substance or analyte is supplied as a gas or vapor. The cell operates at or near atmospheric pressure and contains electrodes energized to produce a voltage gradient along the cell.

Molecules in the sample of air are ionized, such as by means of a radioactive source, an ultraviolet (UV) source, or by corona discharge, and are admitted into the drift region of the cell by an electrostatic gate at one end. The ionized molecules drift to the opposite end of the cell at a speed dependent on the size of the ion. By measuring the time of flight along the cell it is possible to identify the ion. A FAIMS apparatus employs a transverse asymmetric field to filter ions.

Examples of IMS apparatus are described in U.S. Pat. No. 6,051,832, to Bradshaw et al.; U.S. Pat. No. 6,225,623, to Turner et al.; U.S. Pat. No. 5,952,652, to Taylor et al.; United Kingdom Patent No. 2,323,165, to Bradshaw; U.S. Pat. No. 4,551,624, to Spangler et al. U.S. Pat. No. 6,459,079, to Machlinski et al.; U.S. Patent Application Publication No. 2006/249673, to Breach et al.; and U.S. Pat. No. 6,495,824, to Atkinson, all of which are hereby incorporated herein by reference.

In some cases the sensitivity of such apparatus may not be sufficient for reliable detection. Also, the range of analyte concentrations over which an spectrometer apparatus can respond accurately is limited. Depletion of the charge on the reactant ion within the ion source region can cause the apparatus to saturate. This makes it difficult accurately to estimate analyte concentration.

It is accordingly desirable to provide alternative spectrometer apparatus.

SUMMARY OF THE INVENTION

According to one aspect of the present invention, there is provided a spectrometer apparatus of the above-specified kind, characterized in that the spectrometer apparatus is arranged selectively to vary the residence time of ions within the ion source region.

The apparatus may include an arrangement for establishing a voltage gradient in the ion source region, the variation in residence time being provided by varying the voltage gradient. The arrangement for establishing a voltage gradient preferably includes a plurality of electrodes spaced from one another along the ion source region. The apparatus may be arranged to vary the residence time in response to detection of ions, and may be arranged to reduce the residence time in response to an increase in amplitude of an ion peak and to increase residence time in response to a decrease in amplitude of the ion peak.

According to another aspect of the present invention, there is provided a spectrometer apparatus having an ion source region arranged to provide ions to an analyzer region, characterized in that the spectrometer apparatus includes an arrangement for applying a voltage gradient along the length of the ion source region and for varying the voltage gradient in response to detection of ions at the far end of the analyzer region.

According to a further aspect of the present invention, there is provided a method of identifying chemicals in an analyte substance including the steps of subjecting the analyte substance to ionization for a selectively controlled and variable time, subsequently measuring the mobility of the ions of the analyte substance, and deriving an indication of the nature of the ions from their measured mobility.

In a first embodiment, in a spectrometer apparatus having an ion source region arranged to provide ions to an analyzer region, a method which: collects ions in the analyzer region and processes them to provide an output in the form of the spectra of peaks of reactant ions; and varies the residence time of ions in the ion source region in response to at least one characteristic of the spectra of peaks of reactant ions.

In a second embodiment, in a spectrometer apparatus having an ion source region arranged to provide ions to an analyzer region, a method of selectively varying the residence time of the ions within the ion source region which: collects ions passed through the drift region at a far end thereof; processes the collected ions to provide an output in the form of spectra of peaks of reactant ions of varying amplitudes and widths; and varies the residence time of ions within the ion source region based upon at least one of an amplitudes of a particular peak of interest or a group of several peaks or an average over a part or all of the spectra.

In a third embodiment, in a spectrometer apparatus having an ion source region arranged to provide ions of a sample to be analyzed to an analyzer region where they are collected and processed to provide an output, a method of varying the residence time of the ions within the ion source region in response to the output which: establishes a selectively variable voltage gradient or electric field within the ion source region to control the residence time of the ions within the ion source region; processes ions collected in the analyzer region to provide output information indicative of the nature and concentration of an analyte sample; processes the output information to determine the nature and concentration of the sample; and based upon the processed output information, varies the residence time of the ions within the ion source region.

DESCRIPTION OF THE DRAWING

An IMS apparatus that is constructed and operated according to the teachings of the present invention will now be described by way of example, with reference to the accompanying drawing.

The FIGURE shows the spectrometer apparatus of the present invention in schematic form.

DETAILED DESCRIPTION OF THE EXEMPLARY EMBODIMENT

The system includes an IMS drift cell 1 having an inlet port 2 by which sample air to be analyzed is supplied to the apparatus. The port 2 opens into the left-hand end of the interior of the cell 1 via a selective barrier 6 such as a semipermeable membrane, or of any other form that allows passage of the molecules of interest whilst excluding the majority of other molecules. Alternatively, the barrier 6 could be non-selective, such as a pinhole, as described in U.S. Pat. No. 6,502,470, to Taylor et al., which patent is hereby incorporated herein by reference. Instead of a barrier, the sample to be analyzed may be supplied to the cell 1 by some other interface, such as of the kind described in U.S. Pat. No. 5,574,277, to Taylor, which patent is hereby incorporated herein by reference.

The barrier 6 communicates with an ion source region 7 including an ionization source 8 such as a radiation source, UV source or a corona discharge. The ion source region 7 also includes means for producing an electric field directed generally axially of the cell 1. The field is provided by a number of electrodes 9 spaced from one another along the length of the ion source region 7 and connected with a voltage supply 10 in a manner to be described later. To the right of the ion source region 7, a gating grid 11, such as a Bradbury Nielson gate, controls passage of ionized molecules into an analyzer region in the form of a drift region 12 formed by a series of drift electrodes 13 driven by a voltage source 16.

A collector plate 14, behind a grid 15 at the far, right-hand end of the cell 1 collects ions passed through the drift region 12 and provides an output to a processor 20, which also controls the gate 11, the voltage supply 10 and various other functions of the system. The processor 20 provides an output to a display 21, or other utilization means, indicative of the nature and concentration of the sample. Usually this is in the form of spectra of peaks of reactant ions of varying amplitudes and widths.

At its right-hand end, the cell 1 has an inlet 30, by which recirculated, cleaned, dried drift gas is supplied to the interior of the cell where it travels from right to left and flows out via an exhaust outlet 31 close to the gating grid 11 in the ion source region 7. Air is supplied to the inlet 30 by means of a pump 32 having an inlet 33 connected to the exhaust outlet 31 and an outlet 34 connected to a molecular sieve 40, which cleans and dries the air exhausted from the drift chamber 12.

The voltage supply 10 controls the voltage applied to the electrodes 9 in the ion source region 7 such as to produce a selectively variable voltage gradient or electric field along the ion source region. This controls the residence time of ions in the ion source region 7. In practice, when no analyte is detected by the collector plate 14, the voltage supply 10 controls the voltage gradient in the ion source region 7 to be a minimum value so that the ions spend a maximum time within the ion source region. In this way, there is a maximum chance of any analyte ions being ionized by the ion source 8.

When the concentration of analyte increases, this causes a decrease in amplitude of the detected reactant ion peak because ionized analyte molecules have a greater chance of losing their charge as a result of collision with non-ionized molecules. The processor 20 signals the voltage supply 10 to increase the voltage gradient or field within the ion source region 7 so that the ions more quickly away from the ion source 8 to the gating grid 11 and their residence time in the ion source region is reduced. By reducing the residence time of ions in this region 7, there is less chance for the charge on ionized analyte molecules to be depleted by contact with non-ionized molecules, so a greater number of ionized molecules enter the drift chamber 12 and drift to the collector plate 14. This increases the amplitude of ion peaks.

The processor 20 may be arranged to identify a particular ion peak of interest and to control the voltage supply 10 so that the field, and hence the residence time, is varied in response to change in amplitude of that peak. Alternatively, the apparatus may be arranged to vary the residence time in response to the amplitudes of a group of several peaks or an average over a part or all of the spectra. Information about the voltage gradient in the ion source region 7 is preferably used by the processor in determining the concentration of the analyte present, in addition to the reactant ions peak amplitudes.

There are other ways in which a voltage gradient could be established along the ion source region 7 without the need for separate electrodes 9. For example, a voltage could be applied between the ion source 8 and the gating grid 11.

The arrangement of the present invention helps to increase the sensitivity of IMS apparatus over an increased range of analyte concentrations, thereby improving its dynamic concentration range.

The invention is not confined to apparatus in which the residence time is varied by varying an electrical field since there are other ways in which the residence time can be varied selectively, such as by varying the effective length of the ion source region.

The invention is not confined to IMS apparatus but could be applied to other spectrometer apparatus such as FAIMS or DMS apparatus, such as described in International Publication No. WO 2008/035095 A1, to Atkinson et al., which is assigned of record to the assignee of the present patent application and is hereby incorporated herein by reference.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. In a spectrometer apparatus having an ion source region arranged to provide ions to an analyzer region, the method comprising:

collecting ions in the analyzer region and processing them to provide an output in the form of the spectra of peaks of reactant ions; and varying the residence time of ions in the ion source region in response to at least one characteristic of the spectra of peaks of reactant ions.

2. A method as defined in claim 1, wherein the residence time of ions in the ion source region is varied in response to the amplitude of a particular peak of interest.

3. A method as defined in claim 1, wherein the residence time of ions in the ion source region is varied in response to the width of at least one particular peak of interest.

4. A method as defined in claim 1, wherein the residence time of ions in the ion source region is varied in response to the amplitude of a group of several peaks.

5. A method as defined in claim 1, wherein the residence time of ions in the ion source region is varied in response to the amplitude of an average over a part or all of the spectra of peaks of reactant ions.

6. A method as defined in claim 1, wherein the residence time of ions in the ion source region is maintained at a selectively controlled and variable time that was established based upon the spectra of peaks of reactant ions.

7. A method as defined in claim 1, wherein the residence time is reduced in response to an increase in amplitude of an ion peak, and increased in response to a decrease in amplitude of the ion peak.

8. A method as defined in claim 1, wherein a gating grid is located intermediate the ion source region and the analyzer region, and wherein the residence time of ions in the ion source region is varied by varying a voltage gradient established in the ion source region between the ion source and the gating grid.

9. A method as defined in claim 1, wherein a plurality of electrodes that are spaced from one another along the ion source region establish a variable voltage gradient that can be varied to varies the residence time of ions in the ion source region.

10. In a spectrometer apparatus having an ion source region arranged to provide ions to an analyzer region, a method of selectively varying the residence time of the ions within the ion source region, comprising:
collecting ions passed through the drift region at a far end thereof;
processing the collected ions to provide an output in the form of spectra of peaks of reactant ions of varying amplitudes and widths; and
varying the residence time of ions within the ion source region based upon at least one of an amplitudes of a particular peak of interest or a group of several peaks or an average over a part or all of the spectra.

11. A method as defined in claim 10, wherein a gating grid is located intermediate the ion source region and the analyzer region, wherein an arrangement for establishing a voltage gradient is located intermediate the ion source region and the gating grid, and wherein the arrangement for establishing a voltage gradient comprises a plurality of electrodes independent from the gating grid that are spaced from one another along the ion source region.

12. A method as defined in claim 10, wherein the residence time of ions within the ion source region is reduced in response to an increase in the least one of an amplitudes of the particular peak of interest or the group of several peaks or the average over a part or all of the spectra, and increased in response to a decrease in amplitude of the least one of an amplitudes of the particular peak of interest or the group of several peaks or the average over a part or all of the spectra.

13. A method as defined in claim 10, wherein the residence time of ions in the ion source region is varied in response to the amplitude of the least one of an amplitudes of the particular peak of interest or the group of several peaks or the average over a part or all of the spectra.

14. A method as defined in claim 10, wherein the residence time of ions in the ion source region is varied in response to the width of the least one of an amplitudes of the particular peak of interest or the group of several peaks or the average over a part or all of the spectra.

15. In a spectrometer apparatus having an ion source region arranged to provide ions of a sample to be analyzed to an analyzer region where they are collected and processed to provide an output, a method of varying the residence time of the ions within the ion source region in response to the output, the method comprising:
establishing a selectively variable voltage gradient or electric field within the ion source region to control the residence time of the ions within the ion source region;
processing ions collected in the analyzer region to provide output information indicative of the nature and concentration of an analyte sample;
processing the output information to determine the nature and concentration of the sample; and
based upon the processed output information, varying the residence time of the ions within the ion source region.

16. A method as defined in claim 15, wherein the establishing step comprises spacing a plurality of electrodes from one another along the ion source region to establish a variable voltage gradient that can be varied to varies the residence time of ions in the ion source region.

17. A method as defined in claim 15, wherein a gating grid is located intermediate the ion source region and the analyzer region, and wherein the establishing step comprises varying a voltage gradient established in the ion source region between the ion source and the gating grid.

18. A method as defined in claim 15, wherein the processing step comprises processing ions collected in the analyzer region to provide an output in the form of the spectra of peaks of reactant ions.

19. A method as defined in claim 18, wherein the varying step comprises varying the residence time of ions within the ion source region based upon at least one of an amplitudes of a particular peak of interest or a group of several peaks or an average over a part or all of the spectra.

20. A method as defined in claim 18, wherein the residence time is reduced in response to an increase in amplitude of a peak in the at least one of an amplitudes of a particular peak of interest or a group of several peaks or an average over a part or all of the spectra, and increased in response to a decrease in amplitude of the at least one of an amplitudes of a particular peak of interest or a group of several peaks or an average over a part or all of the spectra.

* * * * *